United States Patent
Pai et al.

(10) Patent No.: US 9,384,646 B2
(45) Date of Patent: Jul. 5, 2016

(54) MOTION MONITORING METHOD AND DEVICE

(71) Applicant: Universal Scientific Industrial (Shanghai) Co., Ltd., Shanghai (CN)

(72) Inventors: Huang-Chi Pai, Caotun Township, Nantou County (TW); Jung-Hui Pai, Caotun Township, Nantou County (TW)

(73) Assignee: UNIVERSAL SCIENTIFIC INDUSTRIAL (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 14/536,181

(22) Filed: Nov. 7, 2014

(65) Prior Publication Data

US 2016/0035206 A1  Feb. 4, 2016

(30) Foreign Application Priority Data

Aug. 1, 2014  (TW) .............................. 103126312 A

(51) Int. Cl.
| | |
|---|---|
| G08B 1/08 | (2006.01) |
| G08B 21/04 | (2006.01) |
| A61B 1/00 | (2006.01) |
| G06K 1/00 | (2006.01) |

(52) U.S. Cl.
CPC ............... *G08B 21/0446* (2013.01); *A61B 1/00* (2013.01); *G06K 1/00* (2013.01)

(58) Field of Classification Search
CPC .................................... A61B 1/00; G06K 1/00
See application file for complete search history.

(56) References Cited

U.S. PATENT DOCUMENTS

| 5,157,378 A | 10/1992 | Stumberg et al. |
|---|---|---|
| 8,680,991 B2 | 3/2014 | Tran |
| 2003/0184436 A1 | 10/2003 | Seales et al. |
| 2008/0266118 A1 | 10/2008 | Pierson et al. |
| 2009/0015372 A1* | 1/2009 | Kady .................... G06F 1/26 340/5.54 |
| 2009/0040052 A1 | 2/2009 | Cameron et al. |
| 2010/0081411 A1 | 4/2010 | Montenero |
| 2011/0140913 A1 | 6/2011 | Montenero |
| 2011/0181422 A1* | 7/2011 | Tran .................... G06F 19/3418 340/573.1 |

(Continued)

FOREIGN PATENT DOCUMENTS

| CN | 102298823 A | 12/2011 |
|---|---|---|
| CN | 202553941 | 11/2012 |

(Continued)

OTHER PUBLICATIONS

K-C Shu, "Study of problems and improvements of building facility needs for senior citizens in Taiwan," Theses of Chaoyang University of Technology, May 15, 2013, 58 pp.

*Primary Examiner* — Shirley Lu
(74) *Attorney, Agent, or Firm* — Muncy, Geissler, Olds & Lowe, P.C.

(57) ABSTRACT

Provided is a motion monitoring method for monitoring a user's motion state with a motion monitoring device, sending an alert signal from the motion monitoring device to remind the user and displaying user data for recognizing the user when the motion monitoring device detects that the user's motion state does not generate any variation within a predetermined period of time or a generated variation is less than a standard value, and sending a distress signal from the motion monitoring device to specific and/or nonspecific persons if the alert signal is not turned off after the motion monitoring device having sent the alert signal continuously for a while, so as to lend a helping hand to the user as soon as possible.

12 Claims, 4 Drawing Sheets

(56) References Cited

U.S. PATENT DOCUMENTS

| | | |
|---|---|---|
| 2013/0072765 A1 | 3/2013 | Kahn et al. |
| 2013/0073303 A1* | 3/2013 | Hsu .................... H04L 12/2823 705/2 |
| 2013/0335235 A1 | 12/2013 | Carr et al. |
| 2014/0142403 A1* | 5/2014 | Brumback ......... A61B 5/02433 600/324 |

FOREIGN PATENT DOCUMENTS

| | | |
|---|---|---|
| CN | 202838608 U | 3/2013 |
| TW | M336779 | 7/2008 |
| TW | M400056 | 3/2011 |
| WO | WO 2012/022276 A2 | 2/2012 |
| WO | WO 2014/098765 A1 | 6/2014 |

\* cited by examiner

MOTION MONITORING METHOD AND DEVICE

BACKGROUND OF THE INVENTION

1. Technical Field

The present invention relates to motion state monitoring technology, and more particularly, to a motion monitoring method and a motion monitoring device for use with the method.

2. Description of Related Art

To enable people to measure physiological parameters at home for not only monitoring physiological functions but also dispensing with visits to hospitals for health checks, physiological state monitoring devices were developed and have become instruments indispensable to home care.

Regarding the prior art pertaining to physiological state monitoring devices, U.S. Pat. No. 8,680,991 discloses a wearable device for sending an alert to a user and a distress signal to a specific person (such as a family member of the user) when the user shows no motion for an extended period of time. However, U.S. Pat. No. 8,680,991 has its own limits. For example, after receiving the distress call, the specific person is unlikely to rush home because s/he is far away from home or for any other reason, and thus the specific person has to call an emergency agency which then dispatches paramedics to the user's home—all these take time. Furthermore, China patent 202553941U discloses a wrist-mounted health care device for sending a distress signal as soon as the user falls. However the wrist-mounted health care device seldom stores any user data. As a result, upon their arrival at the user's home, paramedics have to spend much time figuring out what has happened to the physically distressed user, thereby delaying first aid.

BRIEF SUMMARY OF THE INVENTION

The objective of the present invention is to provide a motion monitoring method which involves starting an alert mechanism according to a user's motion variation, sending a distress signal and displaying user-related data if no user feedback motion is detected in the course of the starting of the alert mechanism, so as to lend a helping hand to the user as soon as possible.

In order to achieve the aforementioned objectives, the present invention provides a motion monitoring method which comprises four steps. The first step requires providing a motion monitoring device, wherein the motion monitoring device comprises a monitoring unit, an alert unit, a display unit, and a wireless communication unit. The second step involves mounting the motion monitoring device on a user's body, such that the monitoring unit begins monitoring the user's motion variation. The third step entails sending an alert signal from the alert unit under the control of the monitoring unit to remind the user and displaying a stored user data on the display unit when the monitoring unit detects that the user's motion does not generate any variation within a predetermined period of time or the generated variation is less than a standard value, such that paramedics can quickly recognize the user's identity and evaluate the user's health status. The fourth step entails sending a distress signal from the wireless communication unit under the control of the monitoring unit when the alert unit has been operating for a period of time and not turning off by the user, so as to lend a helping hand to the user as soon as possible.

Preferably, the monitoring unit is a wearable device and comprises a microcontroller, a motion sensor electrically connected to the microcontroller, and a heart rate sensor electrically connected to the microcontroller. The heart rate sensor sends a heart rate sensing signal to the microcontroller as soon as the user puts on the motion monitoring device such that the microcontroller drives the motion sensor to start monitoring the user's motion variation. The heart rate sensor stops sending the heart rate sensing signal to the microcontroller as soon as the user takes off the motion monitoring device such that the microcontroller drives the monitoring unit to enter a power-saving mode.

Preferably, the motion monitoring device further comprises a global positioning unit. If the alert unit has been operating for a period of time and not turning off by the user, the monitoring unit will not only control the wireless communication unit to send the distress signal but will also control the wireless communication unit to send a position signal provided by the global positioning unit.

Another objective of the present invention is to provide a motion monitoring device for use with the motion monitoring method. The motion monitoring device starts an alert mechanism according to the detected user's motion variation so as to catch the user's attention or the other persons' attention and display stored user data such that paramedics or the other persons can evaluate the user's health status quickly. If the alert mechanism has been operating for a period of time and not turning off by the user, the motion monitoring device will send the distress signal so as for the paramedics or the other persons to get first aid as soon as possible.

DETAILED DESCRIPTION OF THE INVENTION

Figure 1:
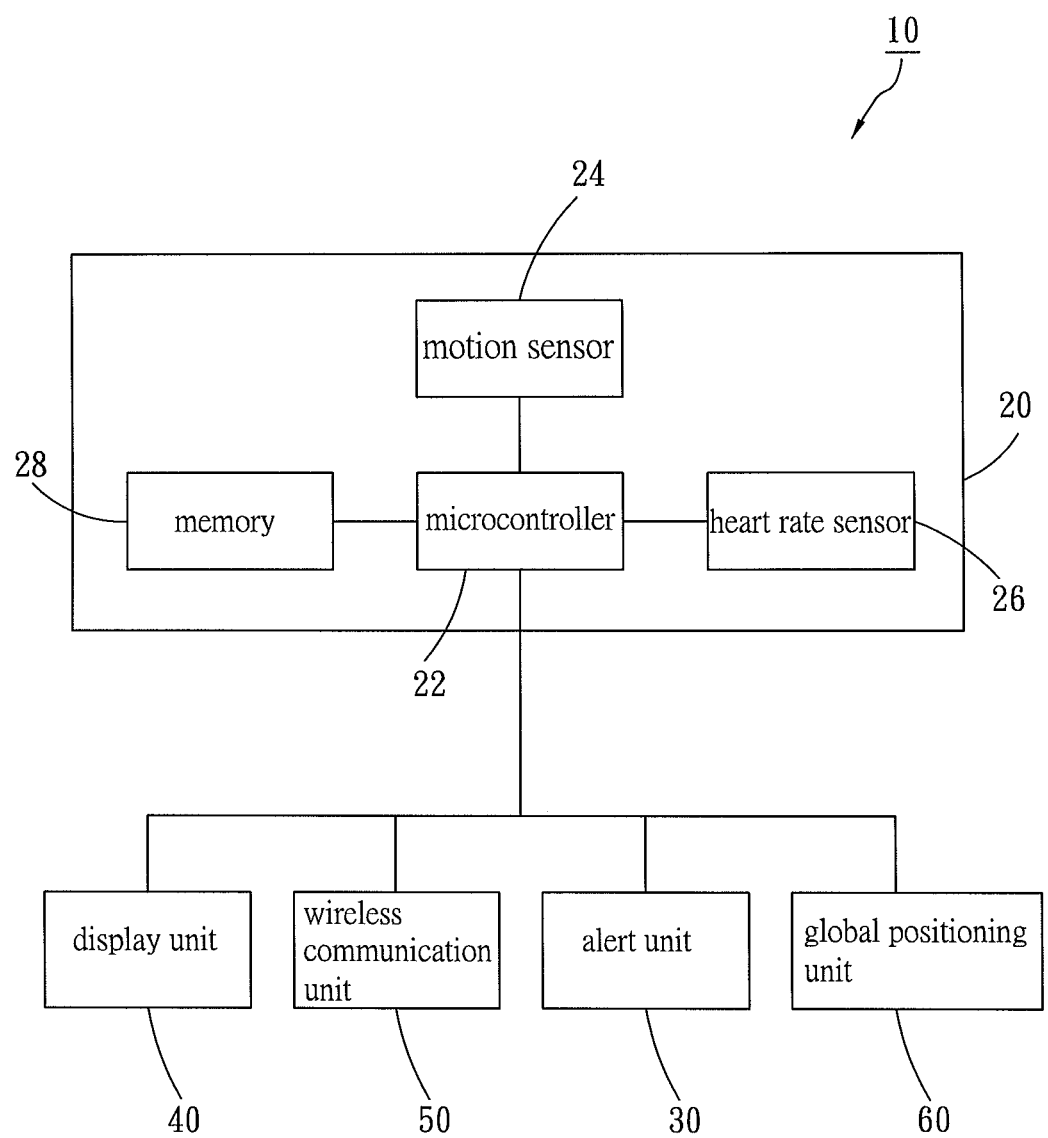
FIG. 1 is a block diagram of a motion monitoring device of the present invention.
Figure 2:
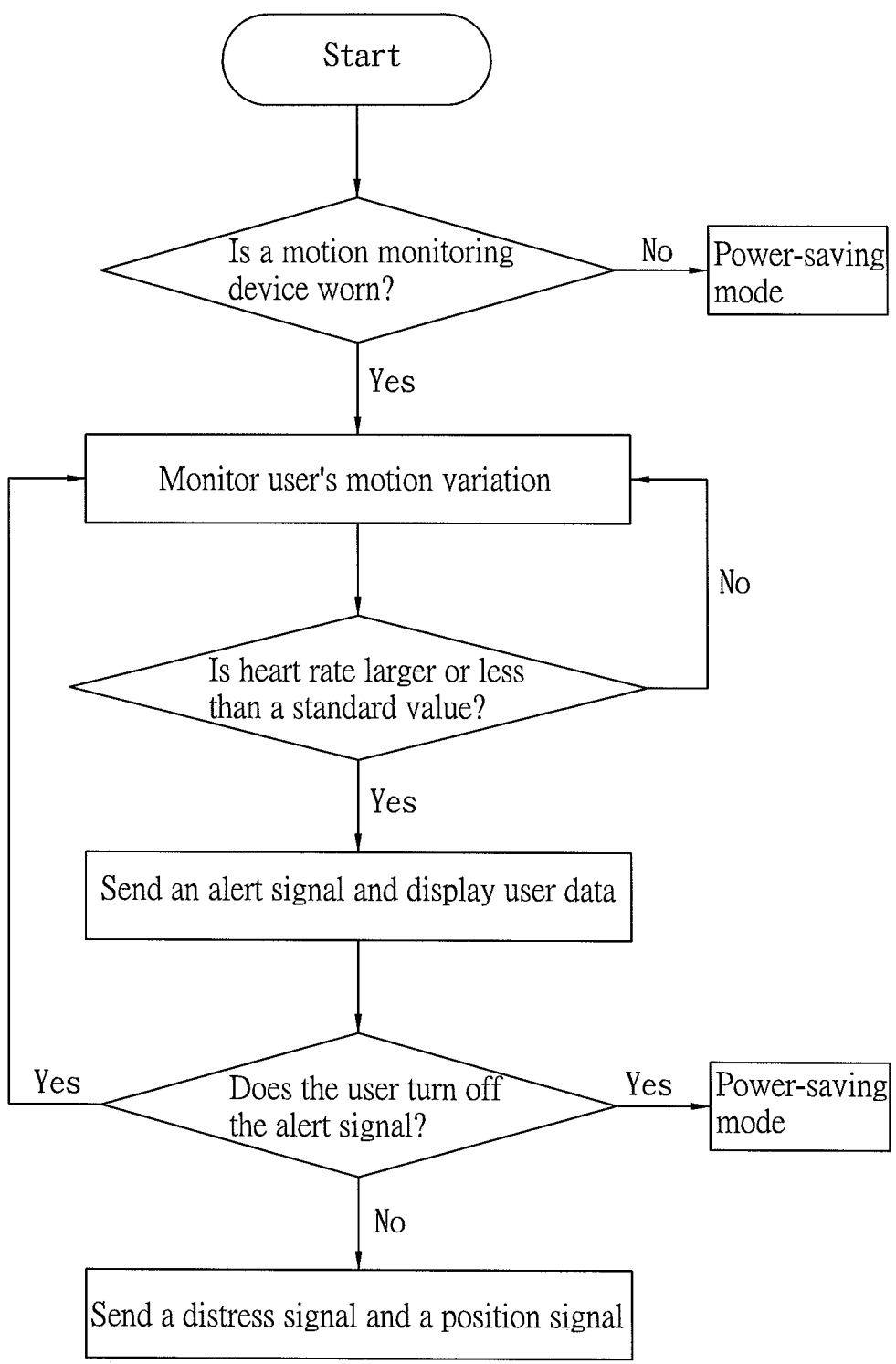
FIG. 2 is a flow chart of the first embodiment of the present invention.

Referring to FIGS. 1, 2, the motion monitoring method of the first embodiment of the present invention comprises the steps described below.

Step a): providing a wearable motion monitoring device 10. Referring to FIG. 1, the motion monitoring device 10 comprises a monitoring unit 20, an alert unit 30, a display unit 40, a wireless communication unit 50 (for example, Wi-Fi, Bluetooth, or GSM), and a global positioning unit 60. The monitoring unit 20 comprises a microcontroller 22, a motion sensor 24, and a heart rate sensor 26. The motion sensor 24 (such as a gyroscope or an accelerometer) is electrically connected to the microcontroller 22 and adapted to sense a user's motion variation. The heart rate sensor 26 is electrically connected to the microcontroller 22 and adapted to sense the user's heart rate variation. The monitoring unit 20 further comprises a memory 28. The memory 28 is electrically connected to the microcontroller 22 and adapted to store user data (such as data pertaining to the user's name, address, emergency contact person, and medical records.)

Step b): wearing the motion monitoring device 10 on the user's body (such as the user's wrist, trunk, or any other appropriate parts) to allow the heart rate sensor 26 of the monitoring unit 20 to start sensing the user's heart rate variation in order to determine whether the user has worn the motion monitoring device 10. When monitoring unit 20 determines that the user has worn the motion monitoring device 10, the heart rate sensor 26 sends a heart rate sensing signal to the microcontroller 22, and then the microcontroller 22 sends a control signal to the motion sensor 24 to cause the motion sensor 24 to start sensing the user's motion variation. Once the user takes off the motion monitoring device 10 or if the user has not yet put on the motion monitoring device 10, the heart rate sensor 26 of the monitoring unit 20 will not detect any heart rate from the user and thus will stop sending a heart rate sensing signal to the microcontroller 22, thereby causing the monitoring unit 20 to enter a power-saving mode.

Step c): when the motion sensor 24 of the monitoring unit 20 detects that the user's motion does not generate any variation within a predetermined period of time or a generated variation is less than a standard value (say 2G, and the standard value can be preset or retrieved from a statistical database), it indicates that the user is either in a state of unconsciousness or a state of motionless activity, and thus the microcontroller 22 of the monitoring unit 20 sends a control signal to the alert unit 30 and the display unit 40, whichever the state the user is in, thereby not only driving the alert unit 30 to send an alert signal (for example, in the form of vibration, buzzing, or flashing light) to remind the user, but also driving the display unit 40 to display the user data. Then, if the user is currently undertaking the motionless activity in a normal situation, the user can turn off the alert signal sent from the alert unit 30. By contrast, if the user is currently undertaking the motionless activity and is reluctant to be subjected to interference, the user can either choose to allow the monitoring unit 20 to keep monitoring motion variation or enter the power-saving mode, or choose to set a specific period of time, say 30 minutes, for beginning to monitor and starting an alert mechanism thereafter, and during the specific period of time the monitoring unit 20 enters the power-saving mode again.

Step d): when the user does not turn off the alert signal which was sent from the alert unit 30 and has been operating for a period of time (preferably 2 minutes), it indicates that the user is in a state of unconsciousness, and in consequence the alert signal sent continuously from the alert unit 30 catches a bystander's attention. Furthermore, a control signal sent from the microcontroller 22 of the monitoring unit 20 drives the wireless communication unit 50 to send a distress signal and a position signal either to nonspecific persons (such as shopkeepers, pedestrians, medical professionals, and police officers) in the vicinity of the user's home or to specific persons (e.g. family members or friends) and the aforesaid nonspecific persons simultaneously, so as to lend a helping hand to the user as soon as possible. Upon paramedics' arrival, the user data displayed on the display unit 40 enables the paramedics to perform first aid optimally on the user as soon as possible. The distress signal is sent by digital message broadcast, telecommunication SMS broadcast, or the like. The position signal is provided by the global positioning unit 60. The user data includes the user's full name, address, and emergency contact person information, and data pertaining to the user's medical records.

Figure 3:
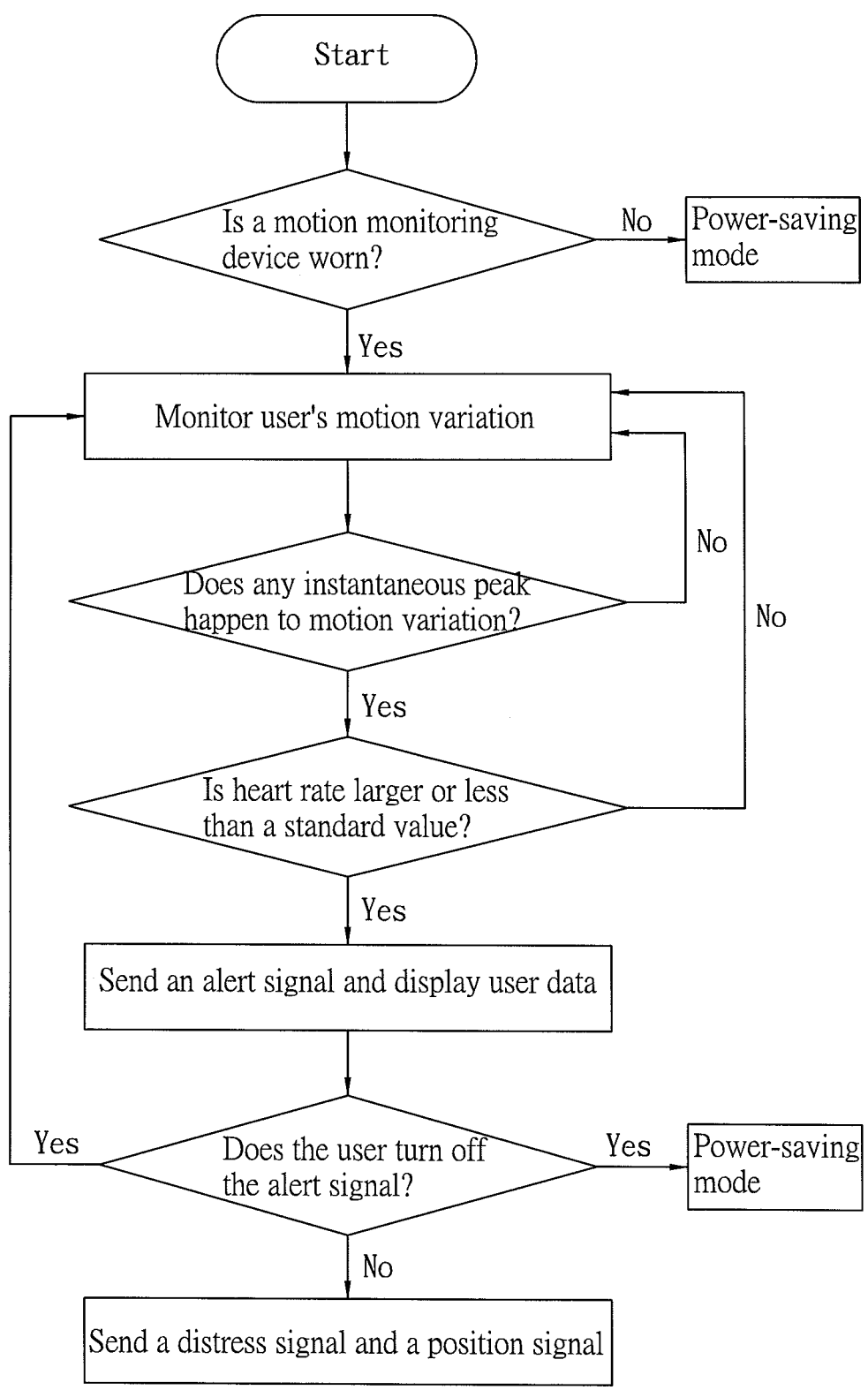
FIG. 3 is a flow chart of the second embodiment of the present invention.

To allow the monitoring unit 20 to be well informed of the user's health status, the monitoring unit 20 is configured with criteria, as shown in FIG. 3. The motion sensor 24 of the monitoring unit 20 senses the user's motion variation to determine whether there is an instantaneous increase in the user's motion variation. Continuous peak variations indicate that the user is currently in motion, such as jogging, exercising or the like; hence, the alert unit 30 does not start. However, if an instantaneous peak value, which is preset according to the user's age and health status or retrieved from a statistical database, is generated, it indicates that the user has fallen or has involved in an accident, and thus the monitoring unit 20 begins to monitor and starts the alert mechanism. If the user is unconscious or sluggish and thus is unable to disable the alert signal, the monitoring unit 20 will automatically send a distress signal carrying position-related information.

Figure 4:
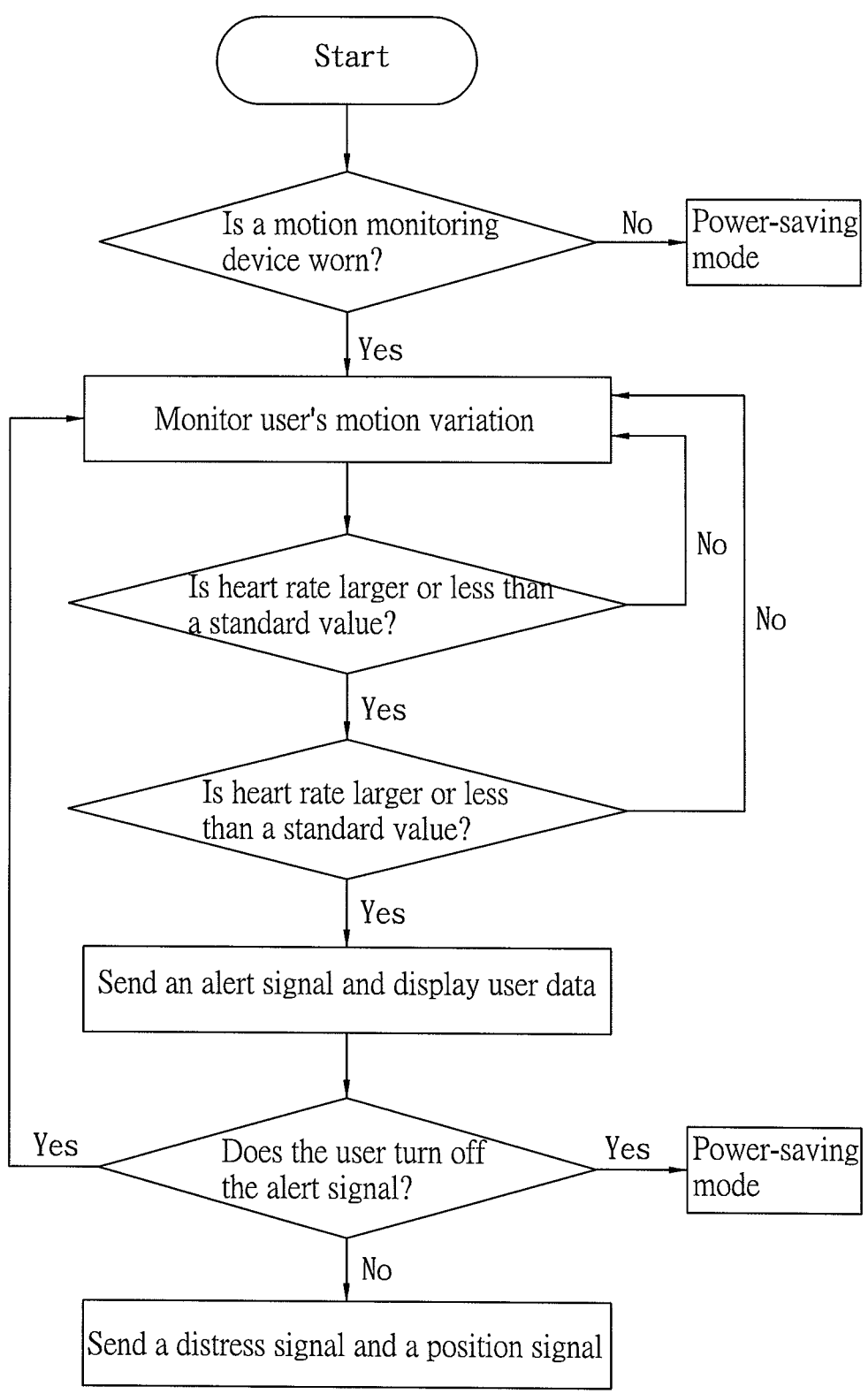
FIG. 4 is a flow chart of the third embodiment of the present invention.

The heart rate sensor 26 of the monitoring unit 20 is configured with an additional criterion (as shown in FIG. 3)—instead of judging an instantaneous peak value of the user's motion variation, the heart rate sensor 26 determines whether the user's heart rate is larger or less than a standard value (for example, larger than 120 bpm or less than 60 bpm) as shown in FIG. 4. The standard value is preset according to the user's age and health status or retrieved from a statistical database. When the determination is affirmative, it indicates that the user is physically distressed to a great extent and thus the user's heart rate increases or decreases abruptly, and thus indicates the need to monitor the user's motion variation and start the alert mechanism again.

Accordingly, the motion monitoring method of the present invention is characterized in that: the alert mechanism is started according to the user's motion variation; and, if the user does not perform any turn-off motion in the course of the starting of the alert mechanism, a distress signal is sent to specific and/or nonspecific persons, and user-related data is displayed, so as to lend a helping hand to the user as soon as possible.

What is claimed is:

1. A motion monitoring method, comprising the steps of:
   a) providing a motion monitoring device, wherein the motion monitoring device comprises a monitoring unit, an alert unit, a display unit, and a wireless communication unit;
   b) wearing the motion monitoring device on a user's body to allow the monitoring unit to start monitoring the user's motion;
   c) sending an alert signal from the alert unit under control of the monitoring unit and displaying on the display unit a user data pertaining to the user's medical records when the monitoring unit detects that the user's motion variation is less than a standard value or unchanged within a predetermined period of time; and
   d) sending a distress signal from the wireless communication unit when the alert unit has been operating for a period of time.

2. The motion monitoring method of claim 1, wherein the monitoring unit comprises a microcontroller and a motion sensor electrically connected to the microcontroller and adapted to monitor the user's motion variation in step c).

3. The motion monitoring method of claim 2, wherein the monitoring unit performs step c) only when the motion sensor senses that the user's motion variation increases instantaneously and is discrete between step b) and step c).

4. The motion monitoring method of claim 2, wherein the monitoring unit further comprises a heart rate sensor electrically connected to the microcontroller, and the monitoring unit performs step c) only when the heart rate sensor of the monitoring unit senses that the user's heart rate is larger or less than a standard value between step b) and step c).

5. The motion monitoring method of claim 2, wherein the monitoring unit further comprises a heart rate sensor electrically connected to the microcontroller and adapted to sense the user's heart rate for determining whether the user has worn the motion monitoring device, wherein, in step b) the heart rate sensor sends a heart rate sensing signal to the microcontroller as soon as the user puts on the motion monitoring device such that the microcontroller drives the motion sensor to start monitoring the user's motion variation, and the heart rate sensor stops sending the heart rate sensing signal to the microcontroller as soon as the user takes off the motion monitoring device such that the microcontroller drives the monitoring unit to enter a power-saving mode.

6. The motion monitoring method of claim 1, wherein, in step d), the monitoring unit controls the wireless communication unit to send the distress signal to specific persons.

7. The motion monitoring method of claim 1, wherein, in step d), the monitoring unit controls the wireless communication unit to send the distress signal to at least a specific person and at least a neighbor nonspecific person simultaneously.

8. The motion monitoring method of claim 1, wherein the motion monitoring device further comprises a global positioning unit for providing a position signal to the monitoring unit in step d).

9. The motion monitoring method of claim 1, wherein, in step d), the wireless communication unit sends the distress signal by one of digital message broadcast and telecommunication SMS broadcast.

10. The motion monitoring method of claim 1, wherein, in step c), after the alert unit has been turned off by the user, the user configures the monitoring unit to enter a power-saving mode.

11. A motion monitoring device for use with the motion monitoring method of claim 1, comprising:

a monitoring unit for monitoring a user's motion, sending a control signal according to the monitored user's motion, and storing a user data pertaining to the user's medical records;

an alert unit electrically connected to the monitoring unit to receive the control signal from the monitoring unit and send an alert signal according to the received control signal;

a display unit electrically connected to the monitoring unit to receive the control signal from the monitoring unit and display the user data pertaining to the user's medical record according to the received control signal; and a wireless communication unit electrically connected to the monitoring unit and adapted to receive the control signal from the monitoring unit, wherein the wireless communication unit sends a distress signal according to the received control signal after the alert unit has been sending the alert signal for a period of time.

12. The motion monitoring device of claim 11, wherein the monitoring unit comprises a microcontroller, a motion sensor, and a heart rate sensor, the microcontroller electrically connected to the alert unit, the display unit, and the wireless communication unit, the motion sensor electrically connected to the microcontroller to sense the user's motion variation, the heart rate sensor electrically connected to the microcontroller to sense the user's heart rate variation, wherein the motion monitoring device enters a power-saving mode if the heart rate sensor does not detect the user's heart rate.

* * * * *